(12) United States Patent
Aduri et al.

(10) Patent No.: US 9,079,156 B2
(45) Date of Patent: Jul. 14, 2015

(54) IONIC FLUIDS

(75) Inventors: Pavan Kumar Aduri, Maharashtra (IN); Parasuveera Uppara, Maharashtra (IN); Uday Ratnaparkhi, Maharashtra (IN); Mangesh Sakhalkar, Maharashtra (IN)

(73) Assignee: RELIANCE INDUSTRIES LTD., Mumbai (IN)

( * ) Notice: Subject to any disclaimer, the term of this patent is extended or adjusted under 35 U.S.C. 154(b) by 109 days.

(21) Appl. No.: 13/878,073

(22) PCT Filed: Jun. 22, 2011

(86) PCT No.: PCT/IN2011/000422
§ 371 (c)(1), (2), (4) Date: Apr. 5, 2013

(87) PCT Pub. No.: WO2012/001703
PCT Pub. Date: Jan. 5, 2012

(65) Prior Publication Data
US 2013/0288886 A1     Oct. 31, 2013

(30) Foreign Application Priority Data
Jun. 29, 2010  (IN) .......................... 1899/MUM/2010

(51) Int. Cl.
| | | |
|---|---|---|
| *B01J 27/138* | (2006.01) | |
| *C07D 213/04* | (2006.01) | |
| *C07F 13/00* | (2006.01) | |
| *C07F 15/02* | (2006.01) | |
| *C07F 1/04* | (2006.01) | |
| *C07F 1/08* | (2006.01) | |
| *C07F 3/06* | (2006.01) | |
| *C07F 5/06* | (2006.01) | |
| *C07F 7/22* | (2006.01) | |
| *H01B 1/12* | (2006.01) | |
| *H01M 10/0566* | (2010.01) | |

(52) U.S. Cl.
CPC ............. *B01J 27/138* (2013.01); *C07D 213/04* (2013.01); *C07F 1/04* (2013.01); *C07F 1/08* (2013.01); *C07F 3/06* (2013.01); *C07F 5/069* (2013.01); *C07F 7/2216* (2013.01); *C07F 13/005* (2013.01); *C07F 15/025* (2013.01); *H01B 1/122* (2013.01); *H01M 10/0566* (2013.01); *H01M 2300/0045* (2013.01)

(58) Field of Classification Search
CPC ................ C07F 1/04; C07F 1/08; C07F 3/06; C07F 5/069; C07F 7/2215; C07F 13/005; C07F 15/026; C07D 213/04; H01B 1/122; B01J 27/138
USPC ........ 556/45, 85, 111, 119, 139, 177; 562/45; 546/347; 502/168
See application file for complete search history.

(56) References Cited

U.S. PATENT DOCUMENTS

| | | |
|---|---|---|
| 4,764,440 A | 8/1988 | Jones et al. |
| 5,731,101 A | 3/1998 | Sherif et al. |
| 5,892,124 A | 4/1999 | Olivier et al. |
| 6,527,977 B2 | 3/2003 | Helber et al. |
| 6,573,405 B1 | 6/2003 | Abbott et al. |
| 7,183,433 B2 | 2/2007 | Abbott et al. |
| 7,196,221 B2 | 3/2007 | Abbott et al. |
| 2005/0147889 A1 | 7/2005 | Ohzuku et al. |
| 2006/0183654 A1 | 8/2006 | Small |
| 2007/0129568 A1 | 6/2007 | Flanagan et al. |
| 2007/0213538 A1 | 9/2007 | Ignatyev et al. |
| 2008/0307703 A1 | 12/2008 | Dietenberger et al. |
| 2009/0247432 A1 | 10/2009 | Miller |

FOREIGN PATENT DOCUMENTS

| | | |
|---|---|---|
| EP | 1322591 B1 | 3/2005 |
| EP | 1165486 B1 | 6/2005 |

OTHER PUBLICATIONS

International Search Report for PCT/B2011/000422 (in English), mailed Dec. 1, 2012; ISA/CN.

*Primary Examiner* — Porfirio Nazario Gonzalez
(74) *Attorney, Agent, or Firm* — Harness, Dickey & Pierce, P.L.C.

(57) ABSTRACT

A method for preparing an ionic compound by mixing at least one compound of formula $C_xA_y\text{-}zH_2O$ (1) with at least one hydrogen donor and heating the mixture obtained is provided. The said ionic compound remains in a physical state selected from the group consisting of liquid and semisolid at a temperature below 150° C., preferably below 125° C.

8 Claims, No Drawings

IONIC FLUIDS

CROSS-REFERENCE TO RELATED APPLICATIONS

This application is a U.S. National Stage of International Application No. PCT/IN2011/000422, filed on Jun. 22, 2011 and published in English as WO/2012/001703 on Jan. 5, 2012. This application claims the benefit of Indian Application No. 1899/MUM/2010, and filed on Jun. 29, 2010. The disclosures of the above applications are incorporated herein by reference.

FIELD OF THE INVENTION

This invention relates to ionic compounds and methods of preparation thereof.

BACKGROUND AND PRIOR ART

This invention relates to ionic compounds and methods for their preparation. In particular the invention relates to ionic compounds which are liquid or semi solid at a temperature below 150° C., preferably below 125° C.

There is a lot of interest in the field of ionic liquids in recent years and scientific publication and number of patent applications in this area are growing at very fast pace. Ionic systems, which are examples of viscous molten salts, have a number of interesting and useful properties, and have utility, for example, as highly polar solvents, co-solvents and catalyst in synthetic chemistry. They also have found to be useful in applications in various fields such as electrochemistry, synthesis of chemicals compounds, dyes, batteries, fuel cells, photovoltaic devices, electrodeposition processes, semi conductor cleaning, pyrolysis, gasification, in applications involving cellulose dissolution, for the electroplating of metals as described, for example in U.S. Pat. No. 6,573,405, U.S. Pat. No. 7,183,433, U.S. Pat. No. 7,196,221, US Patent Appl. No. 2005/0147889, U.S. Pat. No. 6,527,977, US Patent Appl. No. 2008/0307703, US Patent Appl. No. 2006/0183654, US Patent Appl. No. 2009/0247432.

Ionic liquids exhibits very low or no vapour pressure and thus, in contrast to many conventional molecular solvents and are produce virtually no vapours. They are therefore advantageous from a health, safety and environmental point of view.

U.S. Pat. No. 4,764,440 discloses low temperature molten compositions, formed by reacting, for example, trimethylphenylammonium chloride with aluminum trichloride. The resulting ionic compound has a low freezing point (around −75° C.), but suffers from the water sensitivity as EMIC-$AlCl_3$, because of the presence of aluminum trichloride.

Other metal halides, in place of aluminum trichloride are reported, for example, U.S. Pat. No. 5,731,101 discloses the use of iron and zinc halides as the anion portion of an ionic liquid composition. The cation portion is formed by an amine hydrohalide salt, of the formula $R_5N.H.X$. This reference indicates however that the aluminum compounds are preferred, and indeed contains comparative examples which indicate that it is not possible to substitute $SnCl_4$ for aluminum trichloride. Furthermore, it does not suggest the use of quaternary ammonium compounds as cations.

In another disclosure, U.S. Pat. No. 5,892,124 liquid salts of the general formula $Q^+A^-$, wherein $Q^+$ represents quaternary ammonium or phosphonium, and $A^-$ represents a various anions including tetrachloroaluminate, and trichlorozincate are disclosed. Diels-Alder reactions were suggested using the such compounds.

In another relevant disclosure, U.S. Pat. No. 6,573,405, ionic compound formed by the reaction of a quaternary ammonium compound of the formula $R^1R^2R^3R^4N^+X^-$ or a mixture of two or more thereof; with a halide of zinc, tin or iron, or a mixture of two or more thereof are disclosed. Preferably the choline chloride with zinc chloride ionic compound was suggested for applications in electrochemical, electrodeposition, electrochromics and dissolution of metal oxides, battery and Diels-Alder reactions. The examples of the invention teach us in which ionic liquid is prepared from a quaternary ammonium compound (Choline Chloride) and metal halide (zinc chloride) is common except for battery where iron halide was also used.

In yet another relevant disclosure, U.S. Pat. No. 7,183,433, ionic compound formed by the reaction of a quaternary ammonium compound of the formula $R^1R^2R^3R^4N^+X^-$ or a mixture of two or more thereof; with for example with urea. Similarly, attempts were made to form ionic compounds of quaternary ammonium compound of the formula $R^1R^2R^3R^4N^+X^-$ and with specific hydrogen donors belonging to the families, such as carboxylic acids, amides, ethers, esters, aldehydes, ketones, alcohols, carbohydrates. Anions of quaternary ammonium compound of the formula $R^1R^2R^3R^4N^+X^-$ were chloride, nitrate and tetraborate and examples suggest that few ionic liquids were formed with the hydrogen donors, though many of them did not melt till 150° C. Effect of anion $X^-$ was studied with symmetric amine salt by varying the anion. The example in which ionic compound made with urea suggests that asymmetric amine salts are preferred.

In yet another relevant disclosure, U.S. Pat. No. 7,196,221, ionic compound formed by the reaction of a quaternary ammonium compound of the formula $R^1R^2R^3R^4N^+X^-$ or a mixture of two or more thereof; with a hydrated metal salts (chlorides, nitrates, acetates, sulphate salts of) of chromium, calcium, magnesium, cobalt, zinc, copper, lithium, manganese, iron, nickel, cadmium, tin, lead, bismuth, lanthanum, cerium. Ionic liquids of other amine salts, tetraethylammonium chloride, triethylammonium chloride and benzyl trimethylammonium chloride with hydrated chromium chloride were also prepared. The examples teach us ionic compounds prepared in the current disclosure are used in applications of electrochemistry, chemicals synthesis and radical polymerization.

In yet another disclosure US Patent Application No. 2006/0183654, where ionic liquid formed by the reaction of immidazolium, pyridinium, pyrrolidinium, quaternary ammonium and phosphonium compounds with carboxylic acids, amides, sulfates, sulfonates and urea. The invention discloses the use of ionic liquids prepared from immidazolium, pyridinium, pyrrolidinium, quaternary ammonium and phosphonium as cation providing sources with carboxylic acids, amides and urea in semiconductor cleaning processes.

In yet another disclosure US Patent Application No. 2009/0247432, use of ionic liquid formed by the reaction of ammonium compound of the formula $R^1R^2R^3R^4N^+Cl^-$ and $ClR^1R^2R^3R^4N^+Cl^-$ and amides such as urea and carboxylic acids. The disclosure teaches us the use of ionic liquid in dissolving cellulose material from the subterranean region where cellulosic material was used as drilling and fracturing fluid.

DEFINITIONS

As used in the present specification, the following words and phrases are generally intended to have the meanings as set forth below, except to the extent that the context in which they are used indicates otherwise.

The phrase "ionic fluid" is used herein to refer to the solvate prepared whereby ionic compound is dissolved or ionic compound is formed in-situ by dissolving the mixture of salts in solvents.

The phrase "ionic fluid" is used herein to refer to an in situ formed solvated ionic compound in a solvent. The ionic fluid essentially comprises an entity formed by hydrogen bonding between a compound of Formula I and a hydrogen donor compound in the presence of a solvent.

Objects:

It is an object of the present invention to provide a process for preparation of ionic compounds that remain in a liquid or semisolid state at a temperature below 150° C.

It is another object of the present invention to provide a process for preparation of ionic fluids at room temperature.

SUMMARY OF INVENTION

In accordance with one aspect of the present invention, there is provided a process for preparation of an ionic compound that remains in a physical state selected from the group consisting of liquid and semisolid, at a temperature below 150° C., preferably below 125° C., comprising mixing at least one compound of Formula $C_XA_Y.zH_2O$ (I)

wherein,

C is independently selected from the group consisting of Na, K, Li, Mg, Ca, Cr, Mn, Fe, Co, Mo, Ni, Cu, Zn, Cd, Sn, Pb, St, Bi, La, Ce, Al, Hg, Cs, Rb, Sr, V, Pd, Zr, Au, Pt, quaternary ammonium, immidazolium, phosphonium, and pyridinium, pyrrolidinium;

A is independently selected from the group consisting of Cl, Br, F, I, $NO_3$, $SO_4$, $CH_3COO$, HCOO and $C_2O_4$; and z is 0 to 20 with at least one hydrogen donor and heating the resulting mixture to obtain an ionic compound.

Typically, the hydrogen donor is at least one selected from the group consisting of toluene-4-sulphonic acid monohydrate, oxalic acid, maleic acid, citric acid and methane sulfonic acid.

Typically, the mixture is heated to up to 150° C.

In accordance with one embodiment, an ionic fluid is prepared from the ionic compound by dissolving the same in at least one solvent selected from the group consisting of carboxylic acids, amides, alcohols, amines, ketones (aldehydes), esters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride and water, to obtain a clear ionic fluid.

In accordance with another embodiment of the present invention an ionic fluid is prepared in situ by mixing the compound and the hydrogen donor in a solvent at a temperature in the range of 10° C. to 40° C. to obtain a clear ionic fluid that comprises an in-situ formed ionic compound.

Typically, the solvent is at least one selected from the group consisting of selected from the group consisting of carboxylic acids, amides, alcohols, amines, ketones (aldehydes), asters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

In another aspect the present invention provides a clear ionic fluid as prepared by the process as mentioned herein above.

In still another aspect of the present invention, there is provided an ionic compound that remains in a physical state selected from the group consisting of liquid and semisolid, at a temperature at a temperature below 150° C., preferably below 125° C., said ionic compound being obtainable by the reaction of at least one salt of formula I wherein, C is Na, K, Li, Mg, Ca, Cr, Mn, Fe, Co, Mo, Ni, Cu, Zn, Cd, Sn, Pb, St, Bi, La, Ce, Al, Hg, Cs, Rb, Sr, V, Pd, Zr, Au, Pt, quaternary ammonium, immidazolium, phosphonium, pyridinium, pyrrolidinium;

A is Cl, Br, F, I, $NO_3$, $SO_4$, $CH_3COO$, HCOO and $C_2O_4$ and z is 0 to 20 with at least one hydrogen donor selected from the group consisting of toluene-4-sulphonic acid monohydrate, oxalic acid, maleic acid, citric acid and methane sulfonic acid.

DESCRIPTION

The present invention provides a simple process to produce ionic compounds which remain in liquid or semi-solid state at a temperature below 150° C., preferably below 125° C.

The process for preparation of ionic compounds in accordance with the present invention comprises mixing at least one compound of Formula $C_XA_Y.zH_2O$ (I)

wherein,

C is independently selected from the group consisting of Na, K, Li, Mg, Ca, Cr, Mn, Fe, Co, Mo, Ni, Cu, Zn, Cd, Sn, Pb, St, Bi, La, Ce, Al, Hg, Cs, Rb, Sr, V, Pd, Zr, Au, Pt, quaternary ammonium, immidazolium, phosphonium, and pyridinium, pyrrolidinium;

A is independently selected from the group consisting of Cl, Br, F, I, $NO_3$, $SO_4$, $CH_3COO$, HCOO and $C_2O_4$; and z is 0 to 20 with at least one hydrogen donor and heating the resulting mixture to obtain an ionic compound.

The hydrogen donors that are employed in the process accordance with this invention include toluene-4-sulphonic acid monohydrate, oxalic acid, maleic acid, citric acid and methane sulfonic acid.

Typically, the molar ratio of hydrogen bond donor to salt is in the range of 1:1 to 6:1.

Typically, the mixture is heated to a temperature up to about 100-150° C. to obtain the ionic compound.

The formation of ionic compound is the result of formation of hydrogen bond between the anion of the salt and hydrogen donor compound. As the salts mixture starts melting and turns as viscous liquid while heating, effervescence of acidic fumes are observed.

The hydrogen bond formed is relatively strong bond and it is retained even during heating. Acidic fumes are observed. In the wide range of temperatures the effervescence is observed and it depends on the salt that is forming ionic compound with hydrogen bond donor indicating the stability and strength of the hydrogen bond (Angew. Chem. Int. Ed., 2000, 39, 3772-3789, Ionic Liquids—New "Solutions" for Transition Metal Catalysis).

In a further aspect of the present invention there is provided a process for preparation of an ionic fluid. In accordance with one of the embodiments, the ionic fluid is prepared by dissolving the ionic compound obtained by the process of the present invention as described herein above in solvent at a temperature in the range of 10 to 40° C.

In accordance with another embodiment, the ionic fluid is prepared by mixing the ionic compound of the present invention with a solvent and heating to the same to a temperature up to 150° C.

In another embodiment, the hydrogen donor and the compound of Formula I are mixed in a solvent to obtain the ionic fluid of the present invention.

Typically, the solvents employed for preparation of the ionic fluid in accordance with the process of the present invention include carboxylic acids, amides, alcohols, amines, ketones (aldehydes), asters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

The ionic compounds according to the present invention may be utilized for a wide variety of applications in chemical and electrochemical field. The particular applications include solubility of various chemicals such as fatty acids, greases, oils, metals, metals oxides and complexes, cellulose, various organic solvents. The ionic compounds also are used in extraction, surface modification.

Ionic compounds also found to be useful as inert media, as solvents, co-solvents, catalysts or as chemical reagents in the range of temperatures. In other applications, ionic compounds found useful as co-solvent and catalyst where aqueous and non-aqueous polar solvents may be employed. In other application, ionic compound was found to be useful in pure form or dissolved form in aqueous media or non-aqueous media as catalyst or co-solvent for chemical reactions.

Ionic compounds found to be useful as acid catalysts for chemical reactions in both liquid form and immobilized state.

Having described the invention in detail, it is obvious that one skilled in the art will be generally capable of selecting a suitable hydrogen donor for the purpose of the invention, based on the following specific examples herein.

The following examples further illustrate the present invention but are not to be construed as limiting the invention as defined in the claims appended hereto.

The list of combination of hydrogen donor and salts given in Table 1 to 5 demonstrates that most but not all salts are capable of forming ionic compounds or ionic fluids with hydrogen bond donor compounds which are in principle capable of donating or sharing a hydrogen ion to a hydrogen bond.

TABLE 1

Compound I: Hydrogen Donor: Toluene-4-sulphonic acid monohydrate

| Example | Compound II: Salt | Melting Point ° C. |
|---|---|---|
| Chlorides | | |
| 1 | Zinc Chloride | 100 (Softens at 80) |
| 2 | Sodium Chloride | 110 (Softens at 94) |
| 3 | Ferric Chloride | Not melted (softens at 90) |
| 4 | Cobaltous Chloride | Not melted (softens at 80) |
| 5 | Cuprous Chloride | 115 (softens at 87) |
| 6 | Mangenous Chloride | Not melted (softens at 75) |
| 7 | Nickel Chloride | Not melted (softens at 72) |
| 8 | Potassium Chloride | 130 (softens at 90) |
| 9 | Calcium Chloride | Not melted |
| 10 | Stannous Chloride | Not melted (softens at 82) |
| 11 | Cesium Chloride | 84 (softens at 74) |
| 12 | Magnesium Chloride | Not melted |
| 13 | Mercury Chloride | 108 |
| Fluorides | | |
| 14 | Sodium Fluoride | (Not melted (softens at 120) |
| 15 | Calcium Fluoride | Not melted |
| 16 | Potassium Fluoride | (Not melted (softens at 125) |
| 17 | Magnesium Fluoride | (Not melted (softens at 105) |
| Sulphates | | |
| 18 | Sodium Sulphate | 120 (softens at 98) |
| 19 | Zinc Sulphate | (Not melted (softens at 104) |
| 20 | Aluminium Sulphate | (Not melted (softens at 85) |
| 21 | Ammonium Ferric Sulphate | 90 (softens at 40) |
| 22 | Magnesium Sulphate | Not melted (softens at 25) |
| 23 | Calcium Sulphate | 130 (softens at 65) |
| 24 | Ferrous Sulphate | (Not melted (softens at 65) |
| 25 | Cupric Sulphate | (Not melted (softens at 80) |
| 26 | Nickel Sulphate | Not melted (softens at 80) |
| 27 | Potassium Sulphate | 142 (softens at 105) |
| Nitrates | | |
| 28 | Sodium Nitrate | 85 |
| 29 | Aluminium Nitrate | 70 (softens at 45) |
| 30 | Ammonium Nitrate | 85 |
| 31 | Potassium Nitrate | 92 |
| 32 | Nickel Nitrate | Not melted (softens at 25) |
| Bromides | | |
| 33 | Potassium Bromide | 105 |
| 34 | Cobalt Bromide | Not melted (softens at 65) |
| 35 | Cetylpyridinum Bromide | 90 (softens at 70) |
| 36 | Lithium Bromide | Not melted (softens at 130) |
| Acetates | | |
| 37 | Sodium Acetate | Viscous Paste at 25* |
| 38 | Zinc Acetate | (Not melted (softens at 25) |
| 39 | Ammonium Acetate | Viscous Paste at 25* |
| 40 | Cobalt Acetate | (Not melted (softens at 65) |
| 41 | Manganese Acetate | (Not melted (softens at 65) |
| 42 | Lead Acetate | 25 |

TABLE 2

Compound I: Hydrogen Donor: Oxalic Acid

| Example | Compound II: Salt | Melting Point ° C. |
|---|---|---|
| *Chlorides* | | |
| 43 | Zinc Chloride | (Not melted (softens at 25) |
| 44 | Sodium Chloride | 100 |
| 45 | Ferric Chloride | (Not melted (softens at 25) |
| 46 | Cobaltous Chloride | (Not melted (softens at 65) |
| 47 | Cuprous Chloride | (Not melted (softens at 105) |
| 48 | Mangenous Chloride | 95 |
| 49 | Nickel Chloride | (Not melted (softens at 55) |
| 50 | Potassium Chloride | 90 |
| 51 | Calcium Chloride | (Not melted (softens at 95) |
| 52 | Stannous Chloride | 95 (softens at 25) |
| 53 | Cesium Chloride | 75 (softens at 63) |
| 54 | Magnesium Chloride | 65 (softens at 25) |
| 55 | Mercury Chloride | 115 (softens at 110) |
| *Fluorides* | | |
| 56 | Sodium Fluoride | 90 |
| 57 | Calcium Fluoride | (Not melted (softens at 110) |
| 58 | Potassium Fluoride | (Not melted (softens at 75) |
| 59 | Magnesium Fluoride | (Not melted (softens at 120) |
| *Sulphates* | | |
| 60 | Sodium Sulphate | 104 (softens at 92) |
| 61 | Zinc Sulphate | 25 |
| 62 | Aluminium Sulphate | 80 (softens at 65) |
| 63 | Ammonium Ferric Sulphate | 25 |
| 64 | Magnesium Sulphate | 85 |
| 65 | Calcium Sulphate | (Not melted (softens at 120) |
| 66 | Ferrous Sulphate | 50 (softens at 35) |
| 67 | Cupric Sulphate | 25 |
| 68 | Nickel Sulphate | 60 (softens at 50) |
| 69 | Potassium Sulphate | 90 (softens at 80) |
| *Nitrates* | | |
| 70 | Sodium Nitrate | 85 (softens at 75) |
| 71 | Aluminium Nitrate | 60 (softens at 45) |
| 72 | Ammonium Nitrate | 70 |
| 73 | Potassium Nitrate | 80 (softens at 70) |
| 74 | Nickel Nitrate | 70 (softens at 65) |
| *Bromides* | | |
| 75 | Potassium Bromide | 90 |
| 76 | Cobalt Bromide | 100 (softens at 55) |
| 77 | Cetylpyridinum Bromide | Not melted (softens at 90) |
| 78 | Lithium Bromide | 90 (softens paste at 25) |
| *Acetates* | | |
| 79 | Sodium Acetate | 95 (softens at 25) |
| 80 | Zinc Acetate | 78 (softens at 25) |
| 81 | Ammonium Acetate | Not melted (softens at 25) |
| 82 | Cobalt Acetate | Not melted (softens at 70) |
| 83 | Manganese Acetate | 150 (softens at 85) |
| 84 | Lead Acetate | 150 (softens at 60) |

TABLE 3

Compound I: Hydrogen Donor: Maleic acid

| Example | Compound II: Salt | Melting Point ° C. |
|---|---|---|
| *Chlorides* | | |
| 85 | Zinc Chloride | Not melted (softens at 109) |
| 86 | Sodium Chloride | 145 (softens at 110) |
| 87 | Ferric Chloride | 75 (softens at 25) |
| 88 | Cobaltous Chloride | 90 |
| 89 | Cuprous Chloride | 150 (softens at 130) |
| 90 | Mangenous Chloride | 130 |
| 91 | Nickel Chloride | 120 |
| 92 | Potassium Chloride | 145 |
| 93 | Calcium Chloride | 125 |
| 94 | Stannous Chloride | 130 (softens at 90) |
| 95 | Magnesium Chloride | 100 |
| 96 | Mercury Chloride | 150 |
| *Fluorides* | | |
| 97 | Sodium Fluoride | 120 |
| 98 | Calcium Fluoride | Not melted |
| 99 | Potassium Fluoride | 125 |
| 100 | Magnesium Fluoride | 105 |
| *Sulphates* | | |
| 101 | Sodium Sulphate | 150 |
| 102 | Zinc Sulphate | 100 |
| 103 | Ammonium Ferric Sulphate | 65 |
| 104 | Magnesium Sulphate | 115 |
| 105 | Calcium Sulphate | 115 |
| 106 | Cupric Sulphate | 130 |
| 107 | Nickel Sulphate | 140 |
| 108 | Potassium Sulphate | 147 |
| *Nitrates* | | |
| 109 | Sodium Nitrate | 135 |
| 110 | Aluminium Nitrate | 95 (softens at 85) |
| 111 | Ammonium Nitrate | 135 (softens at 85) |
| 112 | Potassium Nitrate | 130 |
| 113 | Nickel Nitrate | 130 (softens at 65) |
| *Bromides* | | |
| 114 | Potassium Bromide | 150 (softens at 140) |
| 115 | Cobalt Bromide | 120 (softens at 60) |
| 116 | Cetylpyridinum Bromide | 105 (softens at 50) |
| 117 | Lithium Bromide | 105 (softens paste at 70) |
| *Acetates* | | |
| 118 | Sodium Acetate | 80 (softens at 60) |
| 119 | Zinc Acetate | 130 |
| 120 | Ammonium Acetate | 80 (softens at 60) |
| 121 | Cobalt Acetate | 65 |
| 122 | Manganese Acetate | 65 |
| 123 | Lead Acetate | 65 |

TABLE 4

Compound I: Hydrogen Donor: Citric Acid

| Example | Compound II: Salt | Melting Point ° C. |
|---|---|---|
| *Chlorides* | | |
| 124 | Zinc Chloride | 80 (softens at 25) |
| 125 | Sodium Chloride | 110 (softens at 65) |
| 126 | Ferric Chloride | 65 (softens at 25) |
| 127 | Cobaltous Chloride | 80 |
| 128 | Cuprous Chloride | 115 (softens at 105) |
| 129 | Mangenous Chloride | 75 |
| 130 | Nickel Chloride | 125 (softens at 65) |
| 131 | Potassium Chloride | 105 (softens at 60) |
| 132 | Calcium Chloride | 142 (softens at 69) |
| 133 | Stannous Chloride | 110 (softens at 60) |
| 134 | Cesium Chloride | 92 (softens at 40) |
| 135 | Magnesium Chloride | 110 |
| 136 | Mercury Chloride | 150 (softens at 69) |
| *Fluorides* | | |
| 137 | Sodium Fluoride | 105 |
| 138 | Calcium Fluoride | 120 |
| 139 | Potassium Fluoride | 100 |
| 140 | Magnesium Fluoride | 70 |

TABLE 4-continued

Compound I: Hydrogen Donor: Citric Acid

| Example | Compound II: Salt | Melting Point ° C. |
|---|---|---|
| Sulphates | | |
| 141 | Sodium Sulphate | 125 (softens at 75) |
| 142 | Zinc Sulphate | 110 (softens at 85) |
| 143 | Aluminium Sulphate | 125 (softens at 105) |
| 144 | Ammonium Ferric Sulphate | 65 (softens at 53) |
| 145 | Magnesium Sulphate | 110 (softens at 80) |
| 146 | Calcium Sulphate | 120 (softens at 110) |
| 147 | Ferrous Sulphate | 90 (softens at 73) |
| 148 | Cupric Sulphate | 106 (softens at 85) |
| 149 | Nickel Sulphate | 60 (softens at 50) |
| 150 | Potassium Sulphate | 90 |
| Nitrates | | |
| 151 | Sodium Nitrate | 125 (softens at 65) |
| 152 | Aluminium Nitrate | 80 (softens at 60) |
| 153 | Ammonium Nitrate | 102 (softens at 25) |
| 154 | Potassium Nitrate | 95 (softens at 85) |
| 155 | Nickel Nitrate | 95 (softens at 65) |
| Bromides | | |
| 156 | Potassium Bromide | 110 (softens at 65) |
| 157 | Cobalt Bromide | 120 (softens at 70) |
| 158 | Cetylpyridinum Bromide | Not melted (softens at 85) |
| 159 | Lithium Bromide | 135 (softens paste at 25) |
| Acetates | | |
| 160 | Sodium Acetate | 25 |
| 161 | Zinc Acetate | 70 |
| 162 | Ammonium Acetate | 100 (softens at 25) |
| 163 | Cobalt Acetate | 85 (softens at 70) |
| 164 | Manganese Acetate | 85 (softens at 70) |
| 165 | Lead Acetate | 70 |

TABLE 5

Compound I: Hydrogen Donor: Methane sulfonicacid

| Example | Compound II: Salt | Melting Point ° C. |
|---|---|---|
| Chlorides | | |
| 166 | Zinc Chloride | 75 (softens at 25) |
| 167 | Sodium Chloride | 105 (softens at 25) |
| 168 | Ferric Chloride | Not melted (softens at 25) |
| 169 | Cobaltous Chloride | 105 (softens at 25) |
| 170 | Cuprous Chloride | 25 |
| 171 | Mangenous Chloride | 75 (softens at 25) |
| 172 | Nickel Chloride | 120 (softens at 25) |
| 173 | Potassium Chloride | 75 (softens at 25) |
| 174 | Calcium Chloride | Not melted (softens at 25) |
| 175 | Stannous Chloride | 65 (softens at 25) |
| 176 | Magnesium Chloride | 75 (softens at 25) |
| 177 | Mercury Chloride | 75 (softens at 25) |
| Fluorides | | |
| 178 | Sodium Fluoride | 141 (softens at 25) |
| 179 | Calcium Fluoride | 25 |
| 180 | Potassium Fluoride | 70 (softens at 25) |
| 181 | Magnesium Fluoride | 120 (softens at 25) |
| Sulphates | | |
| 182 | Sodium Sulphate | Not melted (softens at 25) |
| 183 | Zinc Sulphate | 65 (softens at 25) |
| 184 | Ammonium Ferric Sulphate | 25 |
| 185 | Magnesium Sulphate | 125 (softens at 25) |
| 186 | Calcium Sulphate | 145 (softens at 25) |
| 187 | Cupric Sulphate | 115 (softens at 25) |
| 188 | Nickel Sulphate | 74 (softens at 25) |
| 189 | Potassium Sulphate | 145 (softens at 25) |
| Nitrates | | |
| 190 | Sodium Nitrate | 75 (softens at 25) |
| 191 | Aluminium Nitrate | 145 (softens at 25) |
| 192 | Ammonium Nitrate | 25 |
| 193 | Potassium Nitrate | 110 (softens at 25) |
| 194 | Nickel Nitrate | 130 (softens at 25) |
| Bromides | | |
| 195 | Potassium Bromide | Not melted (softens at 25) |
| 196 | Cobalt Bromide | 80 (softens at 25) |
| 197 | Cetylpyridinum Bromide | 130 (softens at 25) |
| 198 | Lithium Bromide | 70 (softens paste at 25) |
| Acetates | | |
| 199 | Sodium Acetate | 105 (softens at 25) |
| 200 | Zinc Acetate | Not melted (softens at 25) |
| 201 | Ammonium Acetate | 70 (softens at 25) |
| 202 | Cobalt Acetate | 110 (softens at 25) |
| 203 | Manganese Acetate | Not melted |
| 204 | Lead Acetate | 105 (softens at 25) |

Example 1

Toluene-4-sulphonic acid monohydrate, a hydrogen donor was mixed with Zinc chloride in molar ratio of 2:1, in a test tube and mixed with glass rod. A thick viscous paste was formed at room temperature. The viscous paste was heated slowly up to 150° C. and a milky white liquid was observed with effervescence. The ionic compound formed is cooled slowly and just below 95° C., crystal formation starts and on further cooling solid ionic compound was obtained. It demonstrates that hydrogen bond donor compounds which are in principle capable of donating a hydrogen ion to a hydrogen bond. By invention, the compounds which are forming most useful ionic compounds are the ones which melt at or below 150° C. by way of a reaction of a salt or a mixture of two or more thereof; with a hydrogen donor of the formula, or a mixture of two or thereof.

Examples 2-42

Toluene-4-sulphonic acid monohydrate, a hydrogen donor was mixed with a salt (compounds II), in molar ratio of 2:1, as given in Table 1 and having general formula $C_X A_Y \cdot zH_2O$ wherein C is cation, A is anion and z varies from 0 to n depends on hydration of the salt, in a test tube and mixed with glass rod to make uniform mixture. Procedure of example 1 is followed further to form ionic compound. In many but not all the cases, the liquid melt was observed below or near or at 120° C.

Examples 43-84

The procedure of examples 43-84 were followed example 1 except, Oxalic acid is a hydrogen donor instead of Toluene-4-sulphonic acid monohydrate (shown in table 2).

Examples 85-123

The procedure of examples 85-123 were followed example 1 except, Maleic acid is a hydrogen donor instead of Toluene-4-sulphonic acid monohydrate (shown in table 3).

Examples 124-165

The procedure of examples 124-165 were followed example 1 except, Citric acid is a hydrogen donor instead of Toluene-4-sulphonic acid monohydrate (shown in table 4).

Examples 166-204

The procedure of examples 166-204 were followed example 1 except, Methane sulfonicacid is a hydrogen donor instead of Toluene-4-sulphonic acid monohydrate (shown in table 5).

Examples—205-408

The ionic compound formed in examples 1-204, was dissolved in suitable solvents for example water, methanol or DMF to form ionic fluid of respective ionic compound. In some cases but not all, ionic fluid is obtained by filtration of fine suspended solids.

Examples 409-612

Ionic fluid is formed by dissolving at least one of the Hydrogen Donor (compound I) with at least one of the salt (compound II) in suitable solvent for example water or methanol wherein they react to form hydrogen bond in the solvent to form ionic fluid. In many but not all the combinations, wherein solubility of compound I in combination with compound II is soluble or sparingly soluble, hydrogen bond was formed by process of dissolution and formation of ionic fluid. In some cases but not all, ionic fluid is obtained by the filtration of fine suspended solids.

Example—613

The ionic fluids prepared are used for carrying out the dehydration reaction at room temperature, for example 3,4 dimethyl benzaldehyde is reacted with sorbitol to form 3,4-dimethylbenzylidene sorbitol.

The ionic fluid prepared as given in example 1 is dissolved in methanol and 3,4 dimethyl benzaldehyde and sorbitol in 1:1 mole ratio are added to the ionic fluid and stirred for 5 hrs at room temperature. The reaction is stopped after 5 hrs and washed with ether followed by water. The 29% yield was obtained. The product was having 44% diacetal and 56% monoacetal.

Example—614

The ionic fluid prepared as given in example 1 is dissolved in methanol and 3,4 dimethyl benzaldehyde and sorbitol in 2:1 mole ratio are added to the ionic fluid and stirred for 8 hrs at room temperature. The reaction is stopped after 8 hrs and washed with ether followed by water. The 77% yield was obtained. The product was having 92% diacetal and 8% monoacetal.

Example—615

The procedure of example 614 is followed except, the reaction is carried out with the filtrate obtained from example 614 and adding 3,4 dimethyl benzaldehyde and sorbitol in 2:1 mole ratio to the filtrate. The reaction is carried out for 8 hrs and washed with ether followed by water. The 88.5% yield was obtained. The product was having 94% diacetal and 6% monoacetal. This example illustrates the recyclability of ionic fluid for chemical reactions.

Example—616

The ionic fluid prepared as given in example 1 is dissolved in methanol and p-tolualdehyde and sorbitol in 1:1 mole ratio are added to the ionic fluid and stirred for 5 hrs at 26° C. The reaction is stopped after 8 hrs and washed with ether followed by water. The 30% yield was obtained. The product was having 37% diacetal and 63% monoacetal.

Example—617

The ionic fluid prepared as given in example 1, is dissolved in water and added to the ethyl acetate. The 5:1 water to ethyl acetate mole ratio was maintained. The reaction mixture is heated up to 50-55° C. and hydrolysis reaction is carried out for a period of 90 minutes. The reaction is stopped and product is analyzed through gas chromatograph and found the conversion of ethyl acetate to acetic acid and ethanol was in the range of 50-55%.

Example 618

The ionic fluid prepared as given in example 1, is dissolved in n-butanol and added to acetic acid. The 1:1 n-butanol to acetic acid mole ratio was maintained. The reaction is carried out at 26° C. and esterification reaction is carried out for a period of 30 minutes. The reaction is stopped and product is analyzed through gas chromatograph and found the conversion of acetic acid to butyl acetate was in the range of 65-70%.

Example 619

The ionic fluid prepared as given in example 1, carried out an alkylation reaction of olefins with benzene. 25 ml of C10-C11 Paraffin (containing 12% of olefins) and 25 ml of benzene were added to Ionic fluid. The reaction is carried out at 80° C. and reaction is carried out for a period of 30 minutes. The reaction is stopped and product is analyzed through gas chromatograph and found the conversion of olefins to linear alkyl benzenes was in the range of 50%.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

While considerable emphasis has been placed herein on the specific features of the preferred embodiment, it will be appreciated that many additional features can be added and that many changes can be made in the preferred embodiment without departing from the principles of the invention. These and other changes in the preferred embodiment of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A process for preparation of preparing an ionic compound that remains in a physical state selected from the group consisting of liquid and semisolid, at a temperature in the range of 35° C. to 150° C., the process comprising mixing at least one compound of Formula $C_XA_Y \cdot zH_2O$ (I) with at least one hydrogen donor and heating the resulting mixture to obtain an ionic compound;

wherein C is independently selected from the group consisting of Na, K, Li, Mg, Ca, Cr, Mn, Fe, Co, Mo, Ni, Cu, Zn, Cd, Sn, Pb, St, Bi, La, Ce, Al, Hg, Cs, Rb, Sr, V, Pd, Zr, Au, Pt, quaternary ammonium, immidazolium, phosphonium, pyridinium, and pyrrolidinium;

A is independently selected from the group consisting of Cl, Br, F, I, $NO_3$, $SO_4$, $CH_3COO$, HCOO and $C_2O_4$; and z is 0 to 20.

2. The process as claimed in claim 1, wherein the hydrogen donor is at least one selected from the group consisting of toluene-4-sulphonic acid monohydrate, oxalic acid, maleic acid, citric acid and methane sulfonic acid.

3. The process as claimed in claim 1, wherein the mixture is heated up to 150° C.

4. The process as claimed in claim 1, further comprising the method step of dissolving the ionic compound in at least one solvent selected from the group consisting of methanol, ethanol, propan-1-ol, propan-2-ol, 1-butanol, isobutanol, 2-butanol, tert-butanol, dichloromethane, tetrahydrofuran, methyl acetate, ethyl acetate, acetone, di methylformamide, acetonitrile, di methyl sulfoxide, formic acid, acetic acid, methyl ethyl ketone, dimethyl carbonate, diethyl ketone, acetic anhydride, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride and water, to obtain a clear ionic fluid.

5. An ionic compound prepared by the process as claimed in claim 1, that remains in a physical state selected from the group consisting of liquid and semisolid, at a temperature in the range of 35° C. to 150° C., said ionic compound being obtainable by the reaction of at least one salt of formula $C_XA_Y \cdot zH_2O$ (I) with at least one hydrogen donor;

wherein C is independently selected from the group consisting of Na, K, Li, Mg, Ca, Cr, Mn, Fe, Co, Mo, Ni, Cu, Zn, Cd, Sn, Pb, St, Bi, La, Ce, Al, Hg, Cs, Rb, Sr, V, Pd, Zr, Au, Pt, quaternary ammonium, immidazolium, phosphonium, pyridinium, and pyrrolidinium;

A is Cl, Br, F, I, $NO_3$, $SO_4$, $CH_3COO$, HCOO and $C_2O_4$; and

Z is 0 to 20.

6. A process for preparing an ionic compound that remains in a physical state selected from the group consisting of liquid and semisolid, at a temperature in the range of 35° to 150° C., the process comprising mixing at least one compound of Formula $C_XA_Y \cdot zH_2O$ (I) with at least one hydrogen donor in a solvent at a temperature in the range of 10° C. to 40° C. to obtain a clear ionic fluid that comprises an in-situ formed ionic compound;

wherein C is independently selected from the group consisting of Na, K, Li, Mg, Ca, Cr, Mn, Fe, Co, Mo, Ni, Cu, Zn, Cd, Sn, Pb, St, Bi, La, Ce, Al, Hg, Cs, Rb, Sr, V, Pd, Zr, Au, Pt, quaternary ammonium, immidazolium, phosphonium, pyridinium, and pyrrolidinium;

A is independently selected from the group consisting of Cl, Br, F, I, $NO_3$, $SO_4$, $CH_3COO$, HCOO and $C_2O_4$; and z is 0 to 20.

7. The process as claimed in claim 6, wherein the solvent is at least one selected from the group consisting of methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphor amide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

8. A clear ionic fluid prepared by the process as claimed in claim 6.

\* \* \* \* \*